United States Patent
Krishna et al.

(10) Patent No.: US 9,471,974 B2
(45) Date of Patent: Oct. 18, 2016

(54) METHOD AND SYSTEM FOR FEATURE EXTRACTION AND DECISION MAKING FROM SERIES OF IMAGES

(71) Applicants: STC.UNM, Albuquerque, NM (US); SKINfrared LLC, Albuquerque, NM (US)

(72) Inventors: Sanjay Krishna, Albuquerque, NM (US); Sanchita Krishna, Albuquerque, NM (US); Majeed M. Hayat, Albuquerque, NM (US); Pradeep Sen, Albuquerque, NM (US); Maziar Yaesoubi, Albuquerque, NM (US); Sebastian Eugenio Godoy, Albuquerque, NM (US); Ajit Vijay Barve, Albuquerque, NM (US)

(73) Assignees: STC.UNM, Albuquerque, NM (US); SKINfrared LLC, Albuquerque, NM (US)

( * ) Notice: Subject to any disclaimer, the term of this patent is extended or adjusted under 35 U.S.C. 154(b) by 42 days.

(21) Appl. No.: 14/401,827

(22) PCT Filed: Mar. 14, 2013

(86) PCT No.: PCT/US2013/031689
§ 371 (c)(1),
(2) Date: Nov. 17, 2014

(87) PCT Pub. No.: WO2013/172963
PCT Pub. Date: Nov. 21, 2013

(65) Prior Publication Data
US 2015/0187068 A1  Jul. 2, 2015

Related U.S. Application Data

(60) Provisional application No. 61/648,927, filed on May 18, 2012.

(51) Int. Cl.
*G06K 9/00* (2006.01)
*G06T 7/00* (2006.01)
(Continued)

(52) U.S. Cl.
CPC ........... *G06T 7/0012* (2013.01); *G06F 19/321* (2013.01); *G06K 9/46* (2013.01);
(Continued)

(58) Field of Classification Search
USPC ........ 382/100, 103, 106–107, 128–134, 162, 382/168, 173, 181, 199, 209, 220, 232, 254, 382/274, 276, 286–291, 305, 312; 600/504, 600/310, 306, 473; 702/19; 378/4, 21
See application file for complete search history.

(56) References Cited

U.S. PATENT DOCUMENTS

| | | | | |
|---|---|---|---|---|
| 8,918,162 | B2* | 12/2014 | Prokoski | A61B 5/0064 382/128 |
| 2004/0236225 | A1* | 11/2004 | Murphy | A61B 5/015 600/473 |

(Continued)

FOREIGN PATENT DOCUMENTS

KR  10-2012-0041557 A    5/2012

OTHER PUBLICATIONS

"International Application Serial No. PCT/US2013/031689, International Preliminary Report on Patentability mailed Nov. 27, 2014", 9 pgs.

(Continued)

*Primary Examiner* — Seyed Azarian
(74) *Attorney, Agent, or Firm* — Schwegman Lundberg & Woessner, P.A.

(57) ABSTRACT

Apparatus and methods comprise examination of a subject using images of the subject. The images can provide a non-invasive analysis technique and can include a plurality of images of a portion of the subject at different times a temperature stimulus applied to the subject. An image of the portion of the subject can be aligned such that each pixel of the image corresponds to the same point on the subject over a sequence of images of the portion. The sequence of images can be processed after aligning the images such that data is extracted from the images. The extracted data can be used to make decisions regarding the health status of the subject. Additional apparatus, systems, and methods are disclosed.

29 Claims, 4 Drawing Sheets

(51) Int. Cl.
 G06T 3/00 (2006.01)
 G06F 19/00 (2011.01)
 G06K 9/46 (2006.01)
 G06K 9/62 (2006.01)
 A61B 5/00 (2006.01)

(52) U.S. Cl.
 CPC .............. *G06K 9/6267* (2013.01); *G06T 3/00* (2013.01); *G06T 3/0068* (2013.01); *G06T 7/003* (2013.01); *G06T 7/0016* (2013.01); *G06F 19/345* (2013.01); *G06T 2207/10024* (2013.01); *G06T 2207/10048* (2013.01); *G06T 2207/30088* (2013.01); *G06T 2207/30204* (2013.01)

(56) References Cited

U.S. PATENT DOCUMENTS

| | | | |
|---|---|---|---|
| 2006/0173355 A1 | 8/2006 | Alfano et al. | |
| 2007/0173707 A1* | 7/2007 | Mitra | A61B 5/015 600/310 |
| 2009/0234237 A1* | 9/2009 | Ross | A61B 5/026 600/504 |
| 2010/0030083 A1 | 2/2010 | Sanders et al. | |
| 2011/0301441 A1* | 12/2011 | Bandic | A61B 5/0059 600/306 |
| 2012/0101390 A1 | 4/2012 | Iftimia et al. | |
| 2012/0101733 A1* | 4/2012 | Han | G06T 5/50 702/19 |

OTHER PUBLICATIONS

"International Application Serial No. PCT/US2013/031689, International Search Report mailed Jun. 28, 2013", 4 pgs.
"International Application Serial No. PCT/US2013/031689, Written Opinion mailed Jun. 28, 2013", 7 pgs.

* cited by examiner

METHOD AND SYSTEM FOR FEATURE EXTRACTION AND DECISION MAKING FROM SERIES OF IMAGES

CLAIM OF PRIORITY

This patent application is a U.S. National Stage Filing under U.S.C. 371 from International Patent Application Serial No. PCT/US2013/031689 filed 14 Mar. 2013, published as WO/2013/172963A1, which application claims the priority benefit of U.S. Provisional Application Ser. No. 61/648,927, filed 18 May 2012, both of which are incorporated herein by reference in their entirety.

GOVERNMENT INTEREST STATEMENT

This invention was made with U.S. Government support under grant number R25 CA153825 awarded by the National Institute of Health (CNTC). The United States Government has certain rights to the invention.

FIELD OF THE INVENTION

This invention relates generally to the field of non-invasive diagnostics.

BACKGROUND

Skin cancer is a serious medical condition that can be fatal under certain situations if not properly treated. In most cases when this illness is diagnosed, a patient will go to the doctor to report a skin abnormality (discoloration, growth, etc.). After a visual inspection that determines that the abnormality could be malignant, the doctor typically will perform a biopsy, wherein a portion or the entirety of the abnormality is removed. This specimen is then processed with known techniques and examined by an expert to determine whether or not it is a malignant cancer. However, in an effort to conservatively catch all incidents of cancer, doctors tend to perform the biopsy procedure in any case where there is doubt. Therefore, the large majority (>90%) of biopsies that are taken turn out to be healthy tissue. This causes undue suffering and discomfort to healthy individuals. In addition, the risk of not catching serious skin cancers early enough increases when doctors try to avoid this intrusive procedure in the first place.

DESCRIPTION

The following detailed description refers to the accompanying drawings that show, by way of illustration and not limitation, various example embodiments of the invention. These embodiments are described in sufficient detail to enable those skilled in the art to practice these and other embodiments. Other embodiments may be utilized, and structural, logical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

In various embodiments, a complete imaging and analysis system for the detection of skin cancer may offer doctors and medical technicians an entirely passive (non-intrusive) way of detecting skin cancer. Such an imaging and analysis system is based on the principle that healthy tissue has different thermal properties than diseased tissue. For example, when the skin is cooled, healthy tissue will return to its original temperature at a different rate than diseased tissue. By examining these differences, the system can provide doctors a better idea whether the abnormality is or is not malignant. However, such a system or a system similar to an embodiment of a system operable to detect skin cancer may also be used in extremely different applications, such as, for example, but not limit to embodiments of systems to classify minerals in rock for a geological survey.

Figure 1:
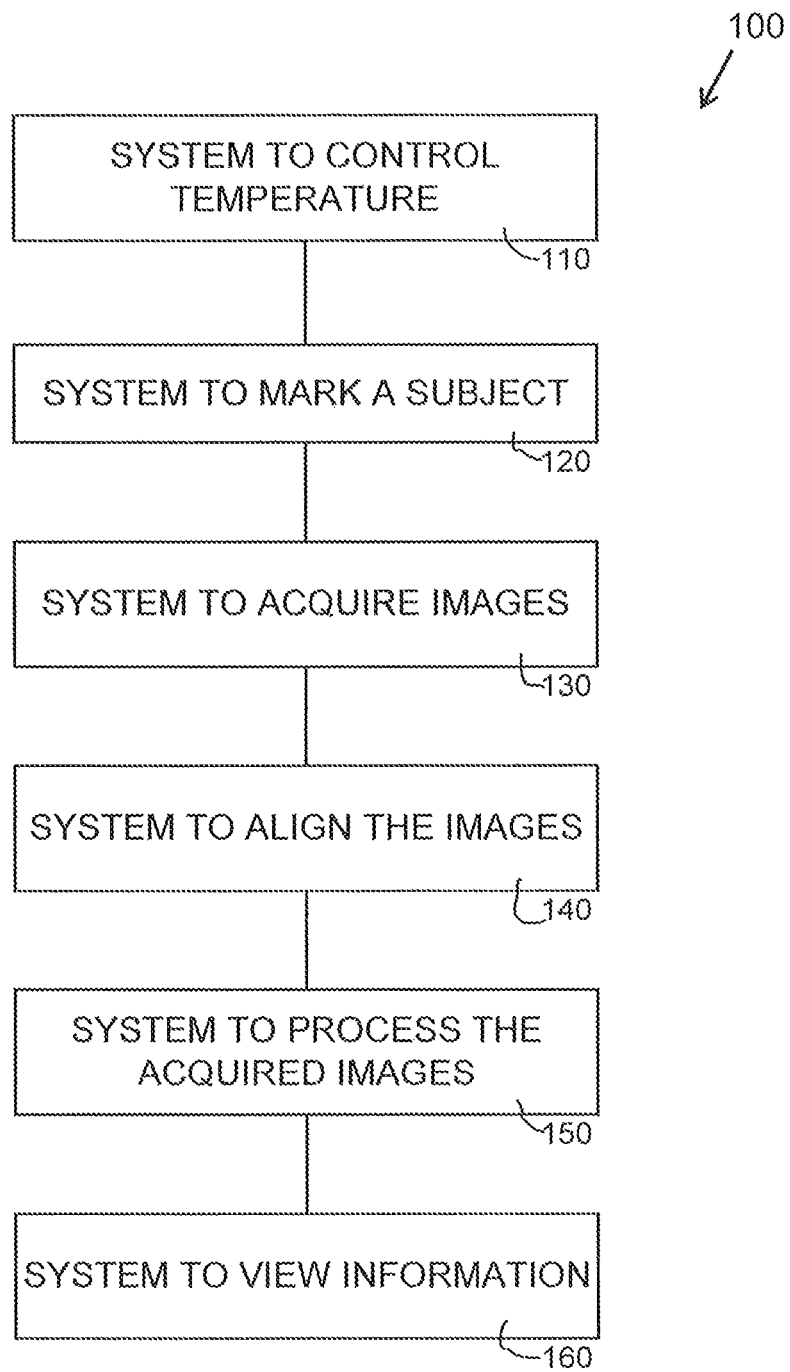
FIG. 1 shows a block diagram of an example imaging and analysis system operable to detect skin cancer, in accordance with various embodiments.

FIG. 1 shows a block diagram of an example embodiment of imaging and analysis system 100 operable to detect skin cancer. System 100 may comprise several components or stages, which may be referred to as systems or subsystems. These systems or subsystems can work together to provide a function of the entire system 100. The stages of system 100 can include a system 110 to control temperature, a system 120 to mark a subject, a system 130 to acquire images, a system 140 to align the images, a system 150 to process the acquired images, and a system 160 to view information. Two or more of the systems can be structured as an integrated system. For example, subsystems of system 100 can be structured as permutations of these systems in an integrated format.

System 110 to control temperature can be arranged as a system for controlling temperature so that the thermal response of a subject can be measured. The subject may be skin of an individual. Controlling temperature can include, for example, cooling a subject, such as skin, from an ambient temperature or from a temperature to which the subject has been heated. System 120 to mark a subject can be arranged as a system for marking the subject, such as skin, to enable a registration process. System 130 to acquire images can be arranged as a system for acquiring images, where the images may be traditional single color images, traditional multi-color images, infrared images, multispectral/hyperspectral images, other types of images or combinations thereof. System 140 to align the images can be arranged as a system for aligning the images with each other to account for subject motion, such as a patient motion and/or camera motion. System 140 to align the images can be structured to operate on stored instructions to align the images according to an algorithm performed by execution of the instructions. An algorithm is herein, and generally, conceived to be a self-consistent sequence of steps, and/or rules governing operation of the steps, leading to a result. The aligning of the images can provide for registering images. System 150 to process the acquired images can be arranged as a system for processing the acquired images to extract information. System 150 to process the acquired images can be structured to operate on stored instructions to process the images according to an algorithm performed by execution of the instructions. System 160 to view information can be arranged as a system for viewing the information in a manner that is meaningful to an expert that deals with the subject being investigation. For system 160 disposed as part of a system to detect cancer, the information can be provided in a manner that is meaningful to a medical expert. Though imaging and analysis systems, as taught herein, may be used in non-medical applications, the following discussions deal with a system operable to detect skin cancer. Such discussions, appropriately modified, may be applied to non-medical applications.

In an embodiment, system 110 to control temperature can be used to detect skin cancer. The detection of skin cancer can be conducted by examining differences in thermal response of different parts of the skin. In other words, a system can use system 110 to control temperature to detect and analyze the rate of warming of skin that has been cooled down. To perform such a function, system 110 to control temperature can include cooling and/or heating components that can cool or warm the skin quickly, while at the same time providing uniform cooling or heating to the region of skin that is being imaged by, for example, system 130 to acquire images. The heating or cooling images can be captured by an infrared camera. System 110 to control temperature may include cooling and/or heating components that not only cool or warm the skin quickly, but can also cool or warm the skin comfortably. Uniformity can be important to have all the cells at the same initial temperature.

In an embodiment, a pressurized air system that blows cold air on the patient's skin can be used. The cooling system may consist of a vortex tube that provides a blast of cold air whose temperature and output volume depend on the system parameters such diameter of opening, shape of nozzle, and inlet pressure. Another approach to cooling or heating can include the use of a thermal spreader to achieve cooling via conduction, convection, or radiation. The thermal spreader could be placed in an on status temporarily and removed before data acquisition or could be in the field of view of an imaging system such as system 130 to acquire images. Pulsed heating or cooling may also be used with different durations to study the differential temperature response of a lesion and healthy skin.

System 120 to mark a subject, such as skin, and system 140 to align the images are related to the process of registering the images acquired using system 130 to acquire images. System 150 to process the acquired images can provide an information extraction process requiring that all of the images are substantially lined up with respect to each other, so that a specific pixel in each image corresponds to the same part of the skin on the patient. In this way, information such as temporal trends at each selected point on the skin's surface can be measured. However, in practice the patient's skin undergoes natural motion (because of breathing, involuntary movement, etc.) and the camera may not be perfectly static. These events produce apparent motion in each of the captured image frames, which must be removed if the information extraction is to be performed successfully.

System 120 to mark a subject can be used to first apply calibration markers to the patient's skin that enable the registration of the images by an algorithm of system 140 to align the images. These are important to a proper working system, since without the calibration markers, it is difficult (if not impossible) to register the images by system 140 to align the images. These markers must be clearly visible against the skin in the wavelength measured by the imaging device, such as a camera, of system 130 to acquire images. In other words, the marker should clearly stand out in the final image when compared to the surrounding skin.

In an embodiment, the marker contains sharp corners that can be clearly resolved in the captured images. These corners can provide features that will help in the registration process when used by an algorithm of system 140 to align the images. It was found experimentally that putting thermal insulation between the marker and the skin helped the marker stand out better in the final infrared (thermal) images. For example, tape can be used as the thermal insulation. Different materials with different emissivity and thermal conductivity can be used to make good markers. For markers to be visible in all frames, markers having a high emissivity can be used in all the frames. Reheating or re-cooling of the surrounding skin from the marker should be avoided. Similarly, reheating or re-cooling of the marker must be avoided.

In an embodiment, system 130 to acquire images can include an imaging device to capture images of the skin's surface. An imaging device can be a camera or other similar device to capture images of the skin's surface. To study the skin's response over time, the camera or similar device includes the capability to acquire video or a sequential series of frames, where the time of each is known or can be computed. In an embodiment, a camera has the capability to acquire frames reasonably close together over a selected time period. The time period may be, but is not limited to, about 3-5 minutes. In a non-limiting example, a camera having the capability to acquire 10 frames per second, for example, for a period of about 3-5 minutes can be used. However, a selected number of frames over a selected time period, other than the above examples, can be implemented, depending on the application. The camera or other imaging device can be arranged to capture an abnormality in the skin being investigated, the skin markers identified by a system, as system 120 to mark a subject, as well as some of the healthy tissue surrounding the abnormality.

The imaging device may be provided in different formats. The imaging device can be an infrared camera, which can measure the temperature of the skin. The imaging device can be a device capable of measuring a response from 300 microns to 3 mm covering the entire electromagnetic spectra. For example, for measuring temperatures, a mid wave infrared camera, for example 5 µm, and a long wave infrared camera, for example 10 µm, can be used.

The imaging device can include a number of different types of cameras. For example, the imaging device can include an infrared camera and a standard color camera. The cameras may both be taking pictures throughout the entire period of the acquisition (either simultaneously or asynchronously). Alternatively, the color camera may capture a single picture with the rest of the acquisition being performed by the infrared camera. Having two kinds of pictures makes the system more useful in practice, since doctors are normally accustomed to looking at color images of the skin and are unfamiliar with infrared images. Therefore, the color images help the doctor recognize the skin features on the infrared images better.

The imaging device, such as a camera, can have spacers or handles to make it easier to align with the skin and to take pictures consistently from a fixed distance to the skin. The imaging devices, such as cameras, can be mechanically, electronically, or optically synced to capture the images at the same point of time.

Stage 140 to align the images can include an algorithm for registering images. The patient's skin will undergo involuntary motion. Since the motion in the series of images is not a desirable feature and must be eliminated, the images acquired over time need to be registered or aligned so that each pixel of the image corresponds to the same point on the skin over the entire sequence. For this reason, a registration algorithm uses the markers from system 120 to align the images to each other. In an embodiment, the algorithm uses a corner detection technique to extract the sharp corners from the image, many of which correspond to the skin markers from using system 120 to mark a subject. Corner detection technique is a known technique. The algorithm treats these sharp corners as features and tracks them over all the frames. The algorithm is structured to use knowledge that these features, although they are moving from frame to frame, all correspond to the same point on the skin surface. Therefore, it solves for a transformation that maps each single feature to its correct location in a reference image. In an example, a homography can be used to compute this transformation, which assumes that the skin is on a plane. Once this transformation has been computed, it can be applied to all the pixels in the image. Sometimes, re-sampling may be performed to compute the final pixel values. Effectively, this registers the skin from one image to another. In an embodiment, with registration performed on the infrared images, the algorithm can work entirely on scalar values. In another embodiment, color images can be registered to the infrared images in a similar manner.

Stage 150 to process the acquired images can use an algorithm for processing the acquired images to extract information. Once the images have been registered, system 150 to process the acquired images performs algorithms on the aligned image sequence in order to extract information. In an embodiment, the information to be extracted is "yes/no" binary values that suggest the presence of malignant cancer. In another embodiment, the information can be a probability value (a real number, not binary) that may indicate the chance of malignancy.

The following provides a non-limiting example of an algorithm to extract information. When using an infrared camera, the temperature of the skin is being imaged at every point in the image over time. Therefore, for each point on the skin, a temperature vs. time curve that indicates how the skin's temperature at that point changed over time can be obtained. A mathematical model can be fitted to this data to generate a list of n parameters that describe the curves at each selected point. The model can be, but is not limited to, a simple polynomial model, an exponential model, a loga-rithmic model, a model using orthogonal basis functions, a model using non-orthogonal basis functions, or a physi-ologically based model. These n parameters can then be used to classify the different parts of the skin with various segmentation/clustering algorithms. It is important to also consider the fact that not all the areas of the skin are at the same initial temperature, which may be due to variations caused by the cooling or heating systems. The algorithm may provide an approach to compensate for the offset associated with the various differential temperature curves.

For example, if a model is fitted with n parameters to each selected point on the skin, each selected point on the skin can essentially be considered as embedded within an n-dimen-sional space. If some parts of the skin are known to be healthy, such as the healthy tissue surrounding the abnor-mality, these parts can be used to potentially classify the points into healthy tissue or malignant tissue. Algorithms such as, but not limited to, principal component analysis (PCA) may be used for such a procedure. PCA effectively would linearly project the n-dimensional parameter space into an orthogonal basis that would separate out features more strongly with fewer parameters.

System 160 to view information can be arranged for viewing the information in a manner that is meaningful to a medical expert. Once the algorithms of stage 150 have been applied to the aligned images, system 160 allows a medical expert to understand the results of the analysis. System 160 can use stored instructions that can be executed by a processor to present the information to the medical expert. For example, executable instructions can be used to plot the temperature trends as a function of a point (or many points) on the skin, where the point(s) are selected by the user using a user selector mechanism such as, but not limited to, a mouse. The executable instructions may assign colors to the representation of the information such that the images can be color-coded using the n-dimensional parameter space dis-covered in stage 150. This procedure may be performed, for example, by producing n false-color images showing the magnitude of each component. Computer vision/machine learning algorithms may also be applied to this data to further segment and highlight features and structures in the data.

In an embodiment, system 160 to view information may provide a visualization system that may include a full mouse-driven navigation control to allow a doctor to rotate the skin to view it from different directions. Also, if the sample is later biopsied, the visualization data can be used to align to the scan of the biopsy to allow for a medical expert to correlate physical features to temperature patterns or other patterns on the skin. This would allow for a greater understanding for the processes involved in malignant cases. In an embodiment, system 160 to view information may be a text-based indicator that indicates to the user "yes" or "no" as to whether to biopsy the sample.

Figure 2:
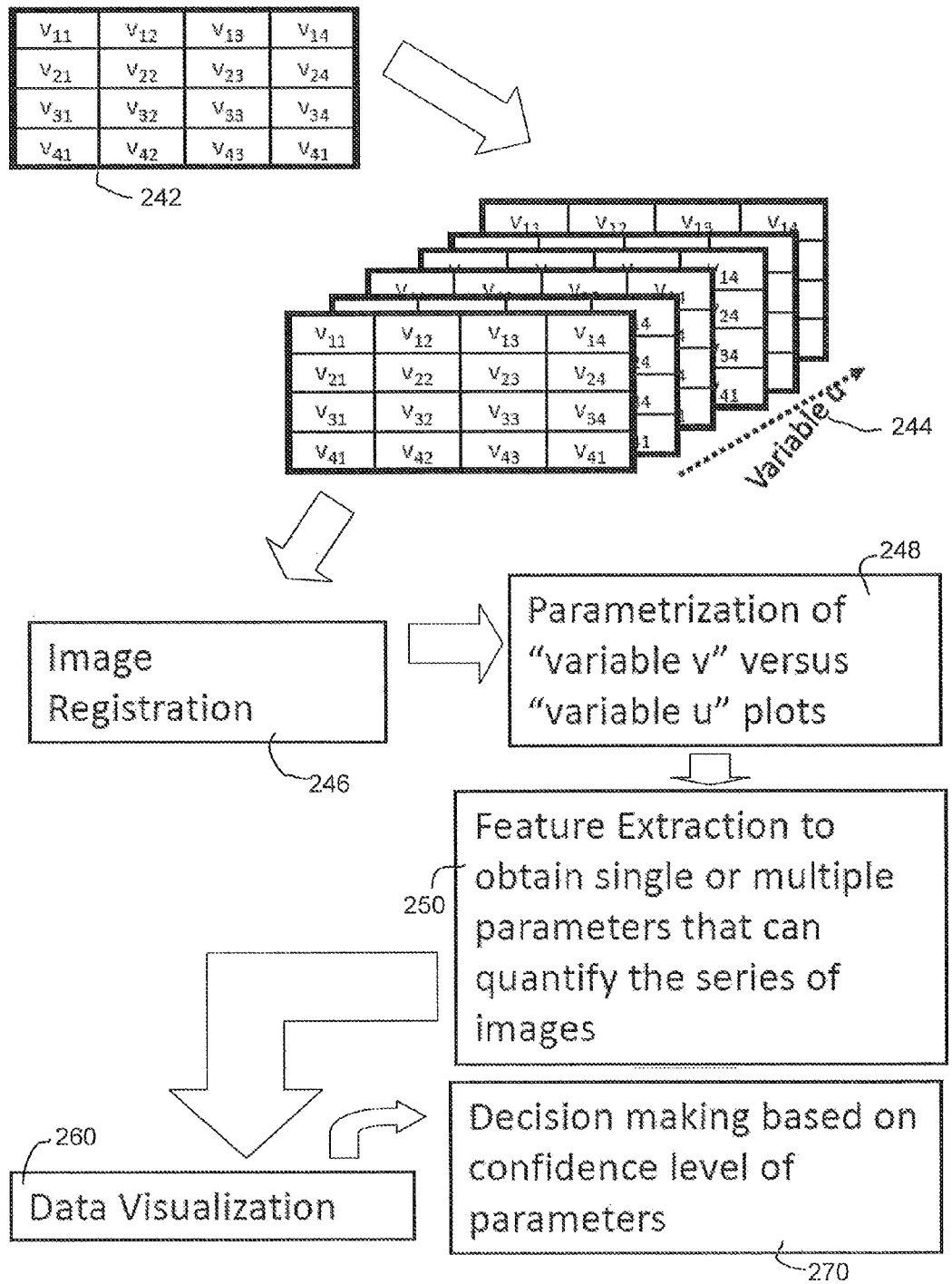
FIG. 2 shows example features of a process flow to make decisions based on images, in accordance with various embodiments.

FIG. 2 shows example features of a process flow to make decisions based on images. At 242, variable v is assigned to each pixel of an image. Though a 4×4 image is shown for presentation purposes, the process flow may be applied to images of different sizes. At 244, pixels with a series of images with variable v changing as a function of variable u are provided. For example, variable v can change as a function of temperature and/or time. Though a 4×4 image is shown for presentation purposes, the process flow may be applied to images of different sizes. At 246, image registra-tion is preformed. At 248, plots of parameterization of variable v versus variable u can be generated. At 250, feature extraction can be performed to obtain single or multiple parameters that can quantify the series of images. At 260, visualization of data from the feature extraction can be performed. At 270, decisions can be made based on confi-dence levels of parameters from the feature extraction and data visualization.

Figure 3:
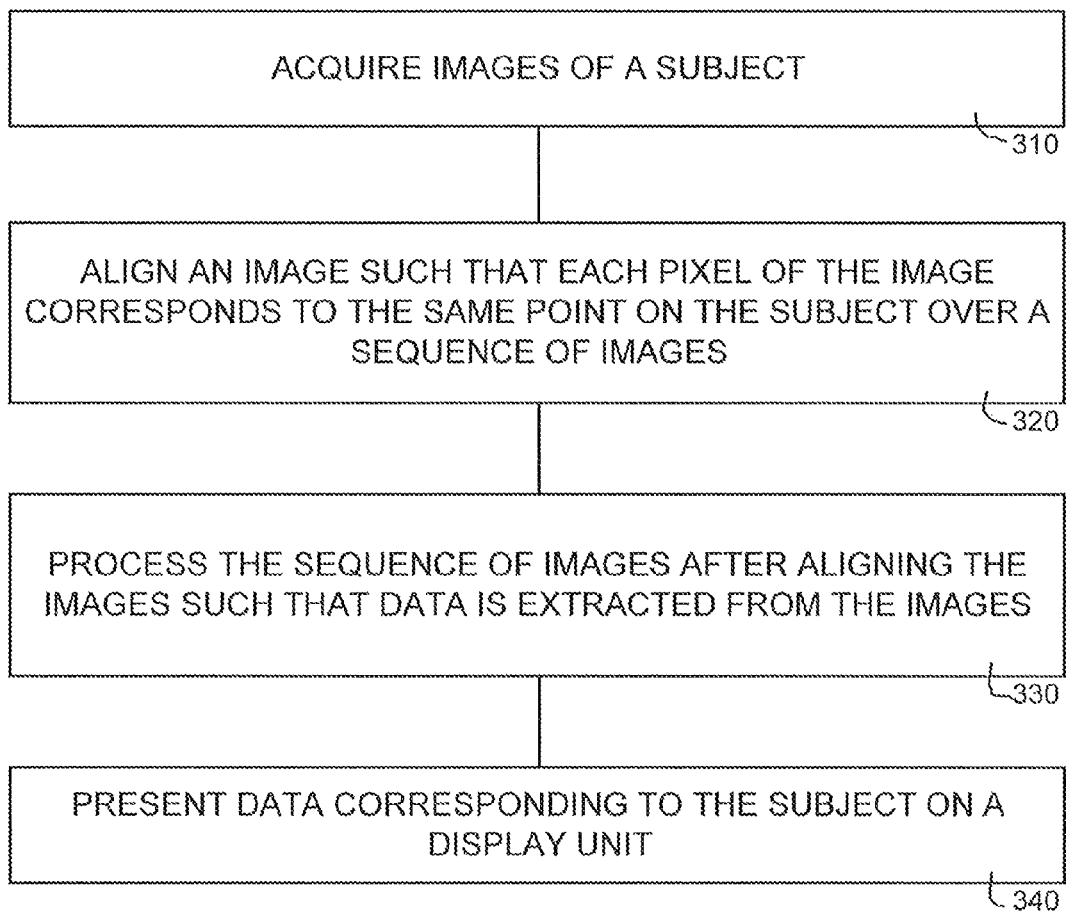
FIG. 3 shows features of an example method of examining a subject using images of the subject, providing a non-invasive analysis technique, in accordance with various embodiments.

FIG. 3 shows features of an embodiment of an example method of examining of a subject using images of the subject, providing a substantially non-invasive analysis technique. The example method may be conducted with a system that includes one or more component systems similar to or identical to the system components of system 100 of FIG. 1 or system 400 of FIG. 4. At 310, images of a subject are acquired. The images can include a plurality of images of a portion of the subject at different times. The portions may be a part of the subject under investigation. For example, the portion may be a lesion on the skin of the subject. The portion may be healthy tissue and tissue under investigation. The portion may include the entire subject. Acquiring the images can include using a plurality of imaging devices. The plurality of imaging devices can include an infrared camera and a camera that provides color images.

At 320, an image is aligned such that each pixel of the image corresponds to a same point on the subject over a sequence of images of the portion. The image being aligned may be an image of the portion of the subject. The method can include applying one or more calibration markers to the subject such that the one or more calibration markers are used when aligning the image of the portion of the subject. The one or more calibration markers can be visible against the portion of the subject in a wavelength range measured by an imagining device that captures the images of the subject. The one or more calibration markers can contain sharp corners resolved in the acquired images, where the one or more calibration markers are used in aligning the image of the portion of the subject. Aligning the image of the portion of the subject can include using a corner detection technique to extract sharp corners from the image. Aligning the image of the portion of the subject can include performing a transformation that maps each feature of the image to its correct location in a reference image. Performing the transformation can use a homography to compute the transformation under an assumption that the subject is on a plane.

At 330, the sequence of images is processed after aligning the images such that data is extracted from the images. Processing the sequence of images may include, for each selected point on the subject, generating temperature vs. time data, fitting a model to the data, generating a list of parameters corresponding to the temperature vs. time data at each selected point using the model, and using one or more segmentation/clustering techniques to classify different parts of the subject. Using one or more segmentation/clustering techniques to classify different parts of the subject can include classifying points on skin as healthy tissue or malignant tissue.

At 340, data corresponding to the subject is presented on a display unit. The data can be presented following the processing of the sequence. Presenting the data can include color-coding the images on the display unit. The color-coding can be conducted using a n-dimensional parameter space generated from processing the sequence of images after aligning the images. Presenting the data can include rotating, on the display unit, an image of a skin subject to view the skin subject from different directions. Presenting the data can include, on the display unit displaying visualization data of a skin subject, aligning the visualization data to a scan of a biopsy of the skin subject corresponding to the visualization data of the skin subject.

The method can include applying a set of temperature stimuli to the portion of the subject, capturing the images of the portion at the different times with respect to applying the set of temperature stimuli, and determining a status of the portion of the subject from processing the sequence of images after alignment. Determining the status of the portion of the subject can include determining a rate of warming the subject after the subject has been cooled. Applying the set of temperature stimuli to the portion of the subject can include applying pulsed heating or cooling with different durations to skin, including healthy skin and a lesion, to analyze a differential temperature response of the lesion and the healthy skin. Determining the status of the portion of the subject can include determining a presence of malignant cancer or a probability value indicating a chance of malignancy. Various techniques discussed herein or combinations thereof can be used in the example method of examining a subject using images of the subject or in other methods to examine a subject using images of the subject in a manner similar to the example method or portions thereof.

In various embodiments, a machine-readable storage device can have instructions stored thereon, which instructions when executed by one or more processors of a machine, cause the machine to perform operations, the operations comprising any of the features of methods of examining a subject using images of the subject and conducting operations based on the images in a manner identical to or similar to the methods and schemes described herein. For example, the instructions can include acquiring images of a subject, the images including a plurality of images of a portion of the subject at different times; aligning an image of the portion of the subject such that each pixel of the image corresponds to a same point on the subject over a sequence of images of the portion; processing the sequence of images after aligning the images such that data is extracted from the images; and presenting data corresponding to the subject on a display unit, following the processing of the sequence. Further, a machine-readable storage device, herein, is a physical device that stores data represented by physical structure within the device. Examples of machine-readable storage devices include, but are not limited to, read only memory (ROM), random access memory (RAM), a magnetic disk storage device, an optical storage device, a flash memory, other electronic, magnetic, and/or optical memory devices, and combinations thereof.

Figure 4:
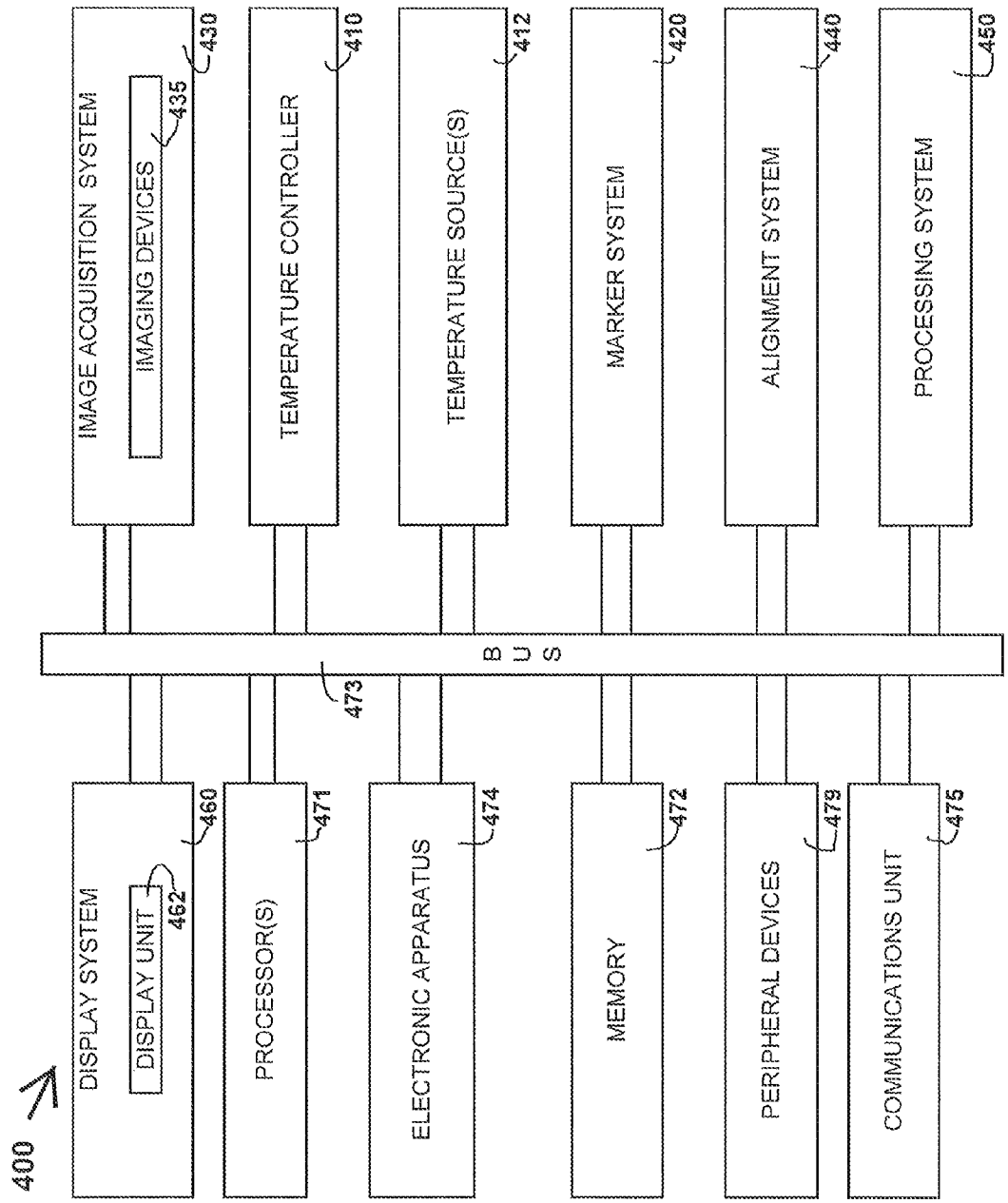
FIG. 4 depicts a block diagram of features of an example system operable to examine a subject using images of the subject, providing a non-invasive analysis technique, in accordance with various embodiments.

FIG. 4 depicts a block diagram of features of an embodiment of an example system 400 operable to examine a subject using images of the subject, providing a non-invasive analysis technique. System 400 can comprise an image acquisition system 430, an alignment system 440, a processing system 450, and a display system 460. Image acquisition system 430 is operable to acquire images of a subject including a plurality of images of a portion of the subject at different times. Image acquisition system 430 may be similar or identical to system 130 to acquire images of FIG. 1. Alignment system 440 is operably coupled to image acquisition system 430, where alignment system 440 is arranged to align images acquired by image acquisition system 430 such that, for each image, each pixel of the image corresponds to a same point on the subject over a sequence of images of the portion. Alignment system 440 may be similar or identical to system 140 to align images of FIG. 1. Processing system 450 is operably coupled to the alignment system and is arranged to process the images, after aligning the images, such that data is extracted from the images. Processing system 450 may be similar or identical to system 150 to process acquired images. Display system 460 is operably coupled to processing system 450. Display system 460 is operable to present data corresponding to the subject on a display unit 462 following the processing of the images.

System 400 can include one or more sources 412 arranged to apply a set of temperature stimuli to the portion of the subject. System 400 can include temperature controller 410 to control operation of sources 412. Temperature controller 410 can be structured to apply pulsed heating or cooling with different durations to skin, including healthy skin and a lesion. This control may be realized with sources 412 in conjunction with circuitry to activate and turn off sources and timing circuitry to control the duration in which sources 412 are on. Temperature sensors can be used with the timing circuitry.

Image acquisition system 430 can be arranged to capture the images of the portion at the different times with respect to application of the set of temperature stimuli using the sources 412. Image acquisition system 430 can include a plurality of imaging devices 435. The plurality of imaging devices 435 can include an infrared camera and a camera that provides color images. Image acquisition system 430 can include one or more imaging devices 435 with one or more optical elements to capture images of the subject. The optical elements can include one or more of a spectral filter, a polarizer, or a neutral density filter. The spectral filter can include a low pass filter, a high pass filter, a bandpass filter, or a notch filter. The polarizer used can have an angle continuously variable from 0 degrees to 360 degrees. The neutral density filter can be operable to change a dynamic range of an image being captured by its corresponding imaging device.

System 400 can include a marker system 420 to identify markers applied to the subject. The markers can be realized as one or more calibration markers applied to the subject in a manner in which alignment system 440 is operable to use to align the image of the portion of the subject. The one or more calibration markers can be structured to be visible against the portion of the subject in a wavelength range measured by an imagining device of image acquisition system 430 that captures the images of the subject. The one or more calibration markers can contain sharp corners resolvable in the acquired images, where the sharp corners can be used in aligning the image of the portion of the subject. Spatial coordinates of a reference marker can be used to correct for voluntary or involuntary movement of a portion of the subject under investigation.

Alignment system 440 can include instructions to perform a corner detection technique to extract sharp corners from the image. Alignment system 440 can include instructions to perform a transformation that maps each feature of the image to its correct location in a reference image. The instructions to perform the transformation can include instructions to use a homography to compute the transformation under an assumption that the subject is on a plane.

Processing system 450 can be structured to be operable to determine a rate of warming a subject after the subject has been cooled. Processing system 450 can be structured to determine a status of the portion of the subject from processing the images after alignment. Processing system 450 can be arranged to analyze a differential temperature response of a lesion and healthy skin of a subject. Processing system 450 can be operable to determine a presence of malignant cancer or a probability value indicating a chance of malignancy. Processing system 450 can include instructions to process the sequence of images including instructions to, for each selected point on the subject, generate temperature vs. time data; to fit a model to the data; to generate a list of discrete and continuous parameters corresponding to the temperature vs. time data at each selected point using the model; and to use one or more segmentation/clustering techniques to classify different parts of the subject. The instructions to use one or more segmentation/clustering techniques can include instructions to classify points on skin as healthy tissue or malignant tissue.

Display system 460 can be structured to be operable to present data with respect to the subject by color-coding the processed images on display unit 462. The color-coding can be conducted using a n-dimensional parameter space generated from processing the sequence of images after aligning the images. Display system 460 can be operable to rotate, on display unit 462, an image of skin of a subject such that the skin is viewable from different directions. Display system 460 can be operable to present the data on display unit 462 displaying visualization data of the skin such that the visualization data is aligned to a scan of a biopsy of the skin corresponding to the visualization data of the skin.

One or more components of system 400 may be realized as one or more sets of instructions stored in system 400, such as stored in memory 472, and executed by one or more processor(s) 471 to perform the functions of such components. Such instructions can include one or more algorithms to perform specific functions. The one or more processor(s) 471 may be used by any of the components of system 400. Alternatively, system components may include their own processor. System 400 may include a database with data disposed in memory 472 that is accessible to the components of system 400. The database can be arranged to store data corresponding to a full body scan of the subject. System 400 can be arranged to conduct non-invasive operations for analysis in accordance with the methods taught herein, and may include various of the devices discussed herein to conduct the non-invasive operations.

System 400 may also include electronic apparatus 474 and a communications unit 475. Electronic apparatus 474 may include circuitry to operate with various components of system 400. For example, electronic apparatus 474 may include circuitry to activate and turn off components, timing circuitry to control the duration in which components are off or on, sensors such as, but not limited to, temperature sensors, or combinations of these circuits and sensors. Communications unit 475 may be operable to provide data and/or analysis results to systems other than system 400.

System 400 can also include a bus 473, where bus 473 provides electrical conductivity among the components of system 400. Bus 473 can include an address bus, a data bus, and a control bus, each may be independently configured. Bus 473 can be realized using a number of different communication mediums that may allow for the distribution of components of system 400. Use of bus 473 can be regulated by processor(s) 471. Bus 473 may be realized as a communications network.

In various embodiments, peripheral devices 479 can include additional displays, additional storage memory, and/or other control devices that may operate in conjunction with processor(s) 471 and/or memory 472. Processor(s) 471 may operate independently depending on an assigned function. Peripheral devices 479 can include a display, which may be arranged as a distributed component, that can be used with instructions stored in memory 472 to implement a user interface to manage the operation of components of system 400. Such a user interface may be operated in conjunction with communications unit 475 and bus 473. The user interface to manage the operation of components of system 400 may be implemented in display system 460.

Systems 110, 120, 130, 140, 150, and 160, combinations thereof, or similar systems, such as but not limited to those of FIG. 4, may be integrated into a system that may provide a "home test" version of systems discussed herein. A person may use this "home test" system in their home routinely to detect if there are possible dangers. The person may be, for example, someone who is in a population that is considered high risk of getting skin cancer, either by their geographical location or skin complexion (fair skin). This kind of system may be able to detect early stages of malignant cancers before they are even visible in the skin, and may produce a warning instructing the person to seek medical help for further examination. This system may also be extended to total body photography, where the differential temperature data is obtained by using an extended cooling system, single or multiple markers, and multiple cameras (infrared, visible etc).

Although specific embodiments have been illustrated and described herein, it will be appreciated by those of ordinary skill in the art that any arrangement that is calculated to achieve the same purpose may be substituted for the specific embodiments shown. Upon studying the disclosure, it will be apparent to those skilled in the art that various modifications and variations can be made in the devices and methods of various embodiments of the invention. Various embodiments can use permutations and/or combinations of embodiments described herein. Other embodiments will be apparent to those skilled in the art from consideration of the specification and practice of the embodiments disclosed herein. It is to be understood that the above description is intended to be illustrative, and not restrictive, and that the phraseology or terminology employed herein is for the purpose of description.

What is claimed is:

1. A method comprising:
    acquiring images of a subject, the images including a plurality of images of a portion of the subject at different times;
    aligning an image of the portion of the subject such that each pixel of the image corresponds to a same point on the subject over a sequence of images of the portion;
    applying one or more calibration markers to the subject such that the one or more calibration markers are used when aligning the image of the portion of the subject, wherein the one or more calibration markers contain sharp corners resolved in the acquired images;
    processing the sequence of images after aligning the images such that data is extracted from the images; and
    presenting data corresponding to the subject on a display unit, following the processing of the sequence, wherein presenting the data includes, on the display unit displaying visualization data of a skin subject, aligning the visualization data to a scan of a biopsy of the skin subject corresponding to the visualization data of the skin subject.

2. The method of claim 1, wherein the method includes:
    applying a set of temperature stimuli to the portion of the subject;
    capturing the images of the portion at the different times with respect to applying the set of temperature stimuli; and
    determining a status of the portion of the subject from processing the sequence of images after alignment.

3. The method of claim 2, wherein determining the status of the portion of the subject includes determining a rate of warming the subject after the subject has been cooled.

4. The method of claim 2, wherein applying the set of temperature stimuli to the portion of the subject includes applying pulsed heating or cooling with different durations to skin, including healthy skin and a lesion, to analyze a differential temperature response of the lesion and the healthy skin.

5. The method of claim 2, wherein determining the status of the portion of the subject includes determining a presence of malignant cancer or a probability value indicating a chance of malignancy.

6. The method of claim 1, wherein acquiring the images includes using a plurality of imaging devices.

7. The method of claim 1, wherein the one or more calibration markers are visible against the portion of the subject in a wavelength range measured by an imagining device that captures the images of the subject.

8. The method of claim 1, wherein aligning the image of the portion of the subject includes using a corner detection technique to extract sharp corners from the image.

9. The method of claim 1, wherein aligning the image of the portion of the subject includes performing a transformation that maps each feature of the image to its correct location in a reference image.

10. The method of claim 9, wherein performing the transformation uses a homography to compute the transformation under an assumption that the subject is on a plane.

11. The method of claim 1, wherein processing the sequence of images includes:
    for each selected point on the subject, generating temperature vs. time data;
    fitting a model to the data;
    generating a list of parameters corresponding to the temperature vs. time data at each selected point using the model; and
    using one or more segmentation/clustering techniques to classify different parts of the subject.

12. The method of claim 11, wherein using one or more segmentation/clustering techniques to classify different parts of the subject includes classifying points on skin as healthy tissue or malignant tissue.

13. The method of claim 1, wherein presenting the data includes color-coding the images on the display unit, using a n-dimensional parameter space generated from processing the sequence of images after aligning the images.

14. The method of claim 1, wherein presenting the data includes rotating, on the display unit, an image of a skin subject to view the skin subject from different directions.

15. A non-transitory machine-readable storage device having executable instructions stored thereon, which instructions when executed, causes a machine to perform operations comprising:
    acquiring images of a subject, the images including a plurality of images of a portion of the subject at different times;
    aligning an image of the portion of the subject such that each pixel of the image corresponds to a same point on the subject over a sequence of images of the portion;
    applying one or more calibration markers to the subject such that the one or more calibration markers are used when aligning the image of the portion of the subject, wherein the one or more calibration markers contain sharp corners resolved in the acquired images;
    processing the sequence of images after aligning the images such that data is extracted from the images; and
    presenting data corresponding to the subject on a display unit, following the processing of the sequence, wherein presenting the data includes, on the display unit displaying visualization data of a skin subject, aligning the visualization data to a scan of a biopsy of the skin subject corresponding to the visualization data of the skin subject.

16. A system comprising:
    an imaging device operable to acquire images of a subject including a plurality of images of a portion of the subject at different times;
    a first processor operably coupled to the imaging device, the first processor arranged to align images acquired by the imaging device such that, for each image, each pixel of the image corresponds to a same point on the subject over a sequence of images of the portion, the first processor arranged to use one or more calibration markers applied to the subject when aligning the image of the portion of the subject, wherein the one or more calibration markers contain sharp corners resolved in the acquired images;

a second processor arranged to process the images, after aligning the images, such that data is extracted from the images, the first and second processors being a set of one or more processors; and a display operably coupled to the second processor, the display operable to present data corresponding to the subject following the processing of the images, wherein presentation of the data includes presentation of visualization data of a skin subject with alignment of the visualization data to a scan of a biopsy of the skin subject corresponding to the visualization data of the skin subject.

17. The system of claim 16, wherein the system includes:
one or more sources arranged to apply a set of temperature stimuli to the portion of the subject;
the imaging device arranged to capture the images of the portion at the different times with respect to application of the set of temperature stimuli; and
the second processor structured to determine a status of the portion of the subject from processing the images after alignment.

18. The system of claim 17, wherein the second processor is operable to determine a rate of warming the subject after the subject has been cooled.

19. The system of claim 17, wherein the system includes a temperature controller to apply pulsed heating or cooling with different durations to skin, including healthy skin and a lesion, the processing system arranged to analyze a differential temperature response of the lesion and the healthy skin.

20. The system of claim 17, wherein the second processor is operable to determine a presence of malignant cancer or a probability value indicating a chance of malignancy.

21. The system of claim 16, wherein the imaging device includes a plurality of imaging devices.

22. The system of claim 16, wherein the one or more calibration markers are visible against the portion of the subject in a wavelength range measured by the imagining device that captures the images of the subject.

23. The system of claim 16, wherein the first processor is operable to execute instructions, stored in a memory, to perform a corner detection technique to extract sharp corners from the image.

24. The system of claim 16, wherein the first processor is operable to execute instructions, stored in a memory, to perform a transformation that maps each feature of the image to its correct location in a reference image.

25. The system of claim 24, wherein the instructions to perform the transformation include instructions to use a homography to compute the transformation under an assumption that the subject is on a plane.

26. The system of claim 16, wherein the second processor is operable to execute instructions, stored in a memory, to process the sequence of images including instructions to:
for each selected point on the subject, generate temperature vs. time data;
fit a model to the data;
generate a list of discrete and continuous parameters corresponding to the temperature vs. time data at each selected point using the model; and
use one or more segmentation/clustering techniques to classify different parts of the subject.

27. The system of claim 26, wherein the instructions to use one or more segmentation/clustering techniques include instructions to classify points on skin as healthy tissue or malignant tissue.

28. The system of claim 16, wherein the display is operable to present the data by color-coding the images on the display.

29. The system of claim 16, wherein the display is operable to rotate an image of a skin subject such that the skin subject is viewable from different directions.

* * * * *